United States Patent
Negoro et al.

(10) Patent No.: US 7,135,567 B2
(45) Date of Patent: Nov. 14, 2006

(54) PROCESSES FOR PRODUCING 2,4,6-TRIS(HYDROXYPHENYL AMINO)-1,3,5-TRIAZINES AND 2,4,6-TRIS(SUBSTITUTED PHENYLAMINO)-1,3,5-TRIAZINES

(75) Inventors: Masayuki Negoro, Minami-ashigara (JP); Ken Kawata, Minami-ashigara (JP)

(73) Assignee: Fuji Photo Film Co., Ltd., Minami-Ashigara (JP)

( * ) Notice: Subject to any disclaimer, the term of this patent is extended or adjusted under 35 U.S.C. 154(b) by 0 days.

(21) Appl. No.: 11/083,216

(22) Filed: Mar. 18, 2005

(65) Prior Publication Data

US 2005/0209453 A1    Sep. 22, 2005

(30) Foreign Application Priority Data

Mar. 19, 2004    (JP)    .............................. 2004-080527

(51) Int. Cl.
    C07D 251/54    (2006.01)
    C07D 251/70    (2006.01)
    C07D 215/44    (2006.01)
    C07D 251/50    (2006.01)
(52) U.S. Cl. ...................... 544/197; 544/217
(58) Field of Classification Search ................ 544/197
    See application file for complete search history.

(56) References Cited

OTHER PUBLICATIONS

Cyanuric Chloride- Encyclopedia of Reagents for Organic Synthesis, edited by Leo Pacquette, pp. 1-15, 2003.*
*Paul De Hoog et al., "New Polydentate and Polynucleating N-Donor Ligands From Amines and 2,4,6-Trichloro-1-3-5-Triazine", Tetrahedron Letters, 2002, pp. 6783-6786, vol. 43 (cited in the specification).

* cited by examiner

Primary Examiner—Venkataraman Balasubramanian
(74) Attorney, Agent, or Firm—Buchanan Ingersoll & Rooney PC

(57) ABSTRACT

A novel process for producing 2,4,6-tris(hydroxyphenyl amino)-1,3,5-triazine is disclosed. The process comprises reacting a compound represented by a formula (I) and a compound represented by a formula (II) in the presence of a base in a mixed solvent of at least one organic solvent and water, to produce a compound represented by a formula (III):

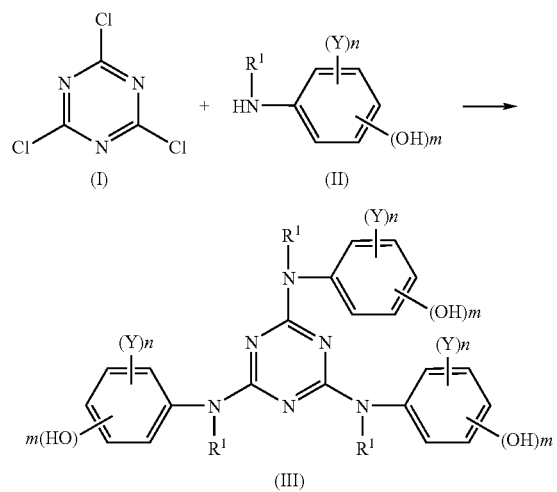

where Y represents a substituent, $R^1$ represents a hydrogen atom or a substituent, m is an integer from 1 to 5, n is an integer from 0 to 4, and when n is 2 or larger, plural Y are same or different each other or plural Y may bond to each other.

11 Claims, No Drawings

PROCESSES FOR PRODUCING 2,4,6-TRIS(HYDROXYPHENYL AMINO)-1,3,5-TRIAZINES AND 2,4,6-TRIS(SUBSTITUTED PHENYLAMINO)-1,3,5-TRIAZINES

CROSS-REFERENCE TO RELATED APPLICATIONS

This application claims benefit of priority under 35 USC 119 to Japanese Patent Application No. 2004-080527 filed Mar. 19, 2004.

TECHNICAL FIELD

The present invention relates to processes for producing 2,4,6-tris(hydroxyphenyl amino)-1,3,5-triazines in high yield with low costs. The present invention relates to processes for producing triazine-ring-containing compounds useful as an ingredient for lubricants or lubricant compositions which can be applied to mechanical friction slide members.

RELATED ART

It is known that 2,4,6-tris(hydroxyphenyl amino)-1,3,5-triazines can be used for a lot of applications, and are useful as industrial intermediates or intermediates of medical products, photographic organic compounds or liquid-crystal materials used for producing electronic-displays.

One known process for producing 2,4,6-tris(hydroxyphenyl amino)-1,3,5-triazines comprises carrying out reaction of cyanuric chloride with 4-amino phenol derivative in an organic solvent in the presence of base. However, according to such a process, it is difficult to control reaction activities of OH group and NH group, which are included in 4-amino phenol derivative, respectively. Another process for producing 2,4,6-tris(4-hydroxyphenylamino)-1,3,5-triazine, using a specific organic solvent in the presence of inorganic base, has been provided (Tetrahedron Letters, 2002, vol. 43, pp. 6783–6786). However, the reaction needs a long time to goes to completion, or hardly goes to completion.

SUMMARY OF THE INVENTION

One object of the present invention is to provide a process for producing 2,4,6-tris (hydroxyphenylamino)-1,3,5-triazines, useful as industrial intermediates, at mild conditions in high yield for a short time. Another object of the present invention is to provide a process for simply producing triazine-ring-containing compounds, useful as ingredients of lubricants, using 2,4,6-tris(hydroxyphenylamino)-1,3,5-triazines.

Under the above circumstances, the present inventors conducted various studies, and as a result, they found that, by carrying out reaction of a base selected from a specific group in a mixed solvent of an organic solvent and water, the target compound can be produced selectively in a high yield for a short time.

In one aspect, the present invention provides a process for producing 2,4,6-tris(hydroxyphenylamino)-1,3,5-triazine comprising reacting a compound represented by a formula (I) and a compound represented by a formula (II) in the presence of a base in a mixed solvent of at least one organic solvent and water, to produce a compound represented by a formula (III):

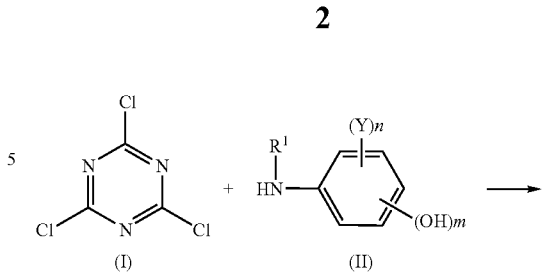

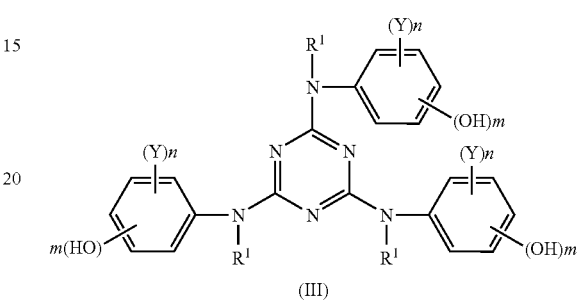

where Y represents a substituent, $R^1$ represents a hydrogen atom or a substituent, m is an integer from 1 to 5, n is an integer from 0 to 4, and when n is 2 or more, plural Y are same or different each other or plural Y may bond to each other.

As embodiments of the present invention, the process wherein the mixed solvent is biphasic at least the time when the reaction is complete; the process wherein the base is an inorganic base; the process wherein at least one kind of alkali metal salt is used as base; the process wherein at least sodium acetate is used as base; and the process wherein the reaction is carried out at a temperature falling within a range from −10° C. to 200° C.; the process wherein the at least one organic solvent is an aprotic solvent; and the process wherein the aprotic solvent is selected from the group consisting of aromatic compounds, ethers, ketones and esters; are provided.

In another aspect, the present invention provides a process for producing 2,4,6-tris(substituted phenylamino)-1,3,5-triazine comprising conversion from a compound represented by a formula (III) into a compound represented by the formula (IV);

Formula (III)

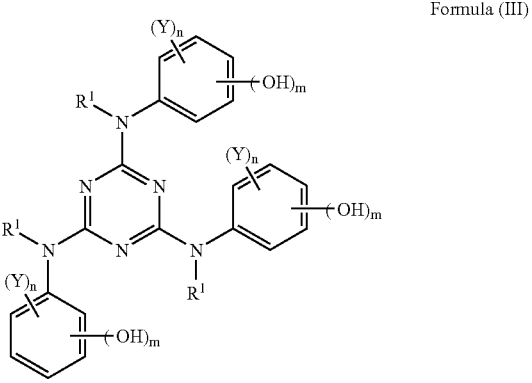

where Y represents a substituent, $R^1$ represents a hydrogen atom or a substituent, m is an integer from 1 to 5, n is an integer from 0 to 4, and when n is 2 or larger, plural Y are same or different each other or plural Y may bond to each other;

Formula (IV)

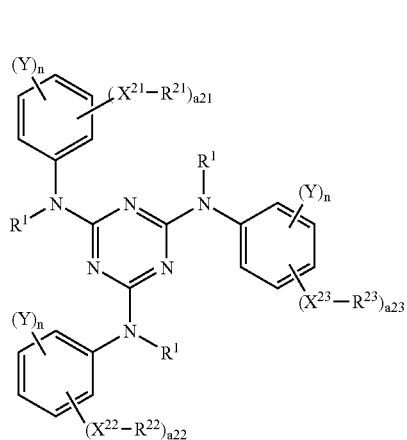

where Y represents a substituent, $R^1$ represents a hydrogen atom or a substituent, $X^{21}$, $X^{22}$ and $X^{23}$ respectively represents a single bond or a divalent linking group selected from the group consisting of $NR^1$ group where $R^1$ represents a hydrogen atom or a $C_{1-30}$ alkyl group, an oxygen atom, a sulfur atom, a carbonyl group, a sulfonyl group and any combinations thereof; $R^{21}$, $R^{22}$ and $R^{23}$ respectively represent a substituent; a21, a22 and a23 respectively represent an integer from 1 to 5 and when a21, a22 or a23 is 2 or larger, plural $X^{21}$–$R^{21}$, plural $X^{22}$–$R^{22}$ or plural $X^{23}$–$R^{23}$ is same or different; and n is an integer from 0 to 4, and when n is 2 or larger, plural Y are same or different each other or plural Y may bond to each other.

As embodiment of the present invention, the process wherein at least one of $X^{21}$, $X^{22}$, $X^{23}$, $R^{21}$, $R^{22}$ and $R^{23}$ contains an ester bond is provided.

According to the present invention, it is possible to provide a process for producing 2,4,6-tris(hydroxyphenylamino)-1,3,5-triazines, useful as industrial intermediates, at mild conditions in high yield for a short time. It is also possible to provide a process for simply producing triazine-ring-containing compounds, useful as ingredients of lubricants, using 2,4,6-tris (hydroxyphenyl amino)-1,3,5-triazines.

DETAILED DESCRIPTION OF THE INVENTION

Hereafter, the present invention will be explained in detail. In the specification, ranges indicated with "to" mean ranges including the numerical values before and after "to" as the minimum and maximum values.

The present invention relates to processes for producing 2,4,6-tris(hydroxyphenylamino)-1,3,5-triazines. The process of the present invention will be described in detail below.

One feature of the process of the present invention resides that a compound represented by a formula (I) is allowed to react with a compound represented by a formula (II) in the presence of base in a mixed solvent of at least one organic solvent and water. The inventors found that carrying out the reaction of a compound represented by the formula (I) and a compound represented by the formula (II) in a mixed solvent of at least one organic solvent and water can reduce the rime for completing the reaction, and improve the selectivity and the yield.

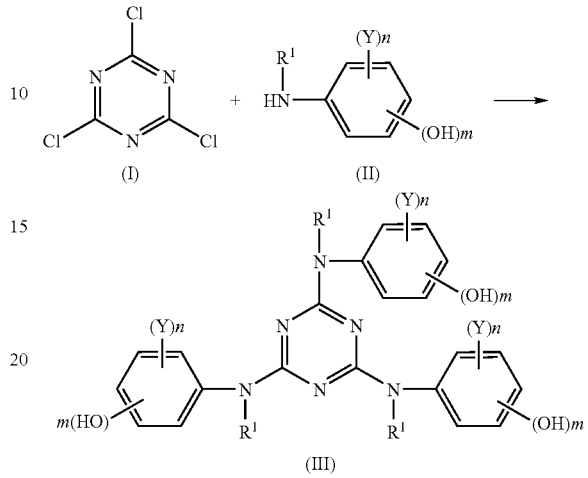

The formulae (II) and (III) will be described in detail. Y represents a substituent. Y is preferably selected from the group consisting of an alkyl group, an aralkyl group, an aryl group, a hetero ring group and an amino group. And m represents an integer from 1 to 5, preferably from 1 to 3 and more preferably 1 or 2. And n represents an integer from 0 to 4, more preferably from 0 to 3 and much more preferably from 0 to 2. When n is 2 or more, plural Y may be same or different each other and bond to each other to form a ring.

$R^1$ represents a hydrogen atom or a substituent. $R^1$ preferably represents a hydrogen atom, an alkyl group, an aralkyl group, an aryl group or a heteroring group; and more preferably represents a hydrogen atom or an alkyl group.

According to the present invention, the reaction of a compound represented by the formula (I) and a compound represented by the formula (II) is carried out in the presence of base. In the specification, the term of "base" is used for any types of inorganic base and any types of organic base. Examples of the inorganic base include sodium carbonate, potassium carbonate, calcium carbonate, sodium hydrogencarbonate, sodium hydroxide, potassium hydroxide, calcium hydroxide, calcium oxide, sodium acetate and potassium acetate. Examples of the organic base include triethylamine, tributylamine, diisopropylethylamine, pyridine, dimethylaminopyridine, N,N-dimethylaniline, and N-methylmorpholine.

According to the process of the present invention, the reaction is carried out in a mixed solvent of at least one organic solvent and water. The mixed solvent may be prepared as a monophasic solvent system in which the organic solvent and water are mixed homogenously, or as a biphasic solvent system in which the organic solvent and water are separated from each other. In some monophasic solvent systems, the separation is occurred gradually with the progress of the reaction, and when the reaction is complete, they become biphasic solvent systems. According to the present invention, such solvent systems can also be used. A mixed solvent, in which two phases are kept from the beginning to the end of the reaction, is preferably used.

Protic or aprotic solvents or any mixture thereof may be used. Aprotic organic solvents are preferred. Examples of the aprotic solvent include nitriles such as acetonitrile, propionitrile and benzonitrile; ethers such as tetrahydrofuran, dioxane and dimethoxyethane; aromatic compounds such as benzene and toluene; halogen solvents such as dichloroethane, chloroform and dichloromethane; esters such as ethyl acetate and butyl acetate; ketones such as acetone, methylethylketone and cyclohexanone. Among these, aromatic compounds, ethers, ketones and esters are preferred, and ketones are more preferred. Among ketones, methylethylketone is much more preferred.

The amount of water used in the process is preferably from 0.01 to 20 times, more preferably from 0.1 to 10 times and much more preferably from 0.5 to 5 times the amount of the organic solvent. The amount of the base is desirably from 1.0 to 10 times, more desirably from 1.0 to 5 times and much more desirably from 1 to 3 times equivalent to the amount of the compound represented by the formula (I). The concentration of the base, desirably selected from inorganic bases, is generally 1 to 80%, preferably from 5 to 80% and more preferably from 10 to 80% with respect to water.

When the compound represented by the formula (I) and the compound represented by the formula (II) are mixed, it is preferred that two solutions of the compound represented by the formula (I) and the compound represented by the formula (II) are prepared respectively and mixed at not higher than 10° C. The mixing may be carried out by adding dropwise a solution of the compound represented by the formula (II) to a solution of the compound represented by the formula (I). After the mixing, a water solution of the base is desirably added to the mixture at not higher than 10° C. After the mixing of the water solution of the base, the reaction is desirably carried out at room temperature, more desirably under heating, and much more desirably under reflux.

According to the process of the present invention, the reaction temperature is not to be limited to any range, and may be carried out at room temperature, or under heating or cooling. Generally, the reaction is preferably carried out at a temperature falling within the range from −10 to 200° C., more preferably at a temperature falling within the range from −10 to 150° C. and much more preferably at a temperature falling within the range from −10 to 120° C. The reaction time is generally from 30 minutes to 10 hours, preferably from 1 to 8 hours and more preferably from 2 to 6 hours.

After the reaction is complete, the obtained reaction mixture may be used without any treatments or may be used after purification in accordance with the intended use. When the reaction mixture is purified, common purification processes such as recrystallization, extraction and chromatography may be carried out.

According to the process of the present invention, 2,4,6-tris (hydroxyphenylamino)-1,3,5-triazines represented by the formula (III) are produced, such compounds are useful as a material of 2,4,6-tris(substituted phenylamino)-1,3,5-triazines represented by a formula (IV) shown below, and 2,4,6-tris(substituted phenylamino)-1,3,5-triazines represented by the formula (IV) are useful as an ingredient of lubricants.

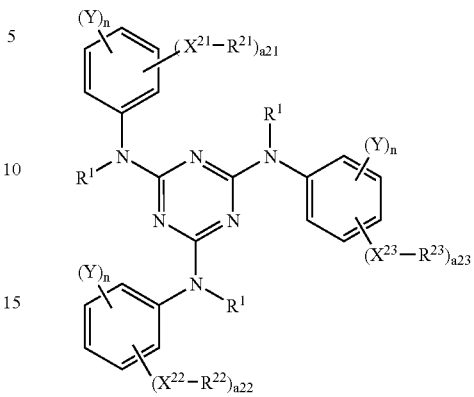

Formula (IV)

In the formula, Y represents a substituent. $R^1$ represents a hydrogen atom or a substituent. $X^{21}$, $X^{22}$ and $X^{23}$ respectively represent a single bond or a divalent group selected from the group consisting of $NR^1$ where $R^1$ represents a hydrogen atom or a $C_{1-30}$ alkyl group, an oxygen atom, a sulfur atom, a carbonyl group, a sulfonyl group and any combination thereof. In the formula, $R^{21}$, $R^{22}$ and $R^{23}$ respectively represent a substituent. In the formula, a21, a22 and a23 respectively represent an integer from 1 to 5 and when a21, a22 or a23 is 2 or larger, plural $X^{21}$–$R^2$, plural $X^{22}$–$R^{22}$ or plural $X^{23}$–$R^{23}$ is same or different. In the formula, n is an integer from 0 to 4 and when n is 2 or larger, plural Y are same or different each other or plural Y may bond to each other.

In the formula (IV), the definitions of Y, $R^1$ and n are respectively same as those in the formula (III), and their preferred scopes are respectively same as those in the formula (III).

In the formula (IV), it is preferred that $R^{21}$, $R^{22}$ and $R^{23}$ respectively represents an alkyl group, an aralkyl group, an aryl group, a heterocyclic group or an amino group; it is more preferred that they respectively represent a $C_{1-20}$ linear, branched or cyclic alkyl group such as methyl, ethyl, isopropyl, n-butyl, 2-ethylhexyl and cyclohexyl; a $C_{7-20}$ aralkyl group such as benzyl, phenethyl and naphthylmethyl; a $C_{6-20}$ aryl group such as phenyl and naphthyl; or a $C_{5-20}$ heterocyclic group such as pyridyl and quinolyl.

The alkyl group, aralkyl group, aryl group or heterocyclic group represented by $R^{21}$, $R^{22}$ or $R^{23}$ may have at least one substituent. Examples of the substituent include an alkyl group such as methyl, ethyl, propyl, isopropyl, butyl, isobutyl and pentyl; an alkoxy group such as methoxy, ethoxy, methoxyethoxy, n-butyloxy, n-octyloxy and benzoyloxy; an aryloxy group such as phenoxy and naphthoxy; an aryl group such as phenyl and naphthyl; an acyl group such as acetyl and benzoyl; a halogen atom such as chlorine, bromine, fluorine and iodine; a cyano group, a nitro group, a silyl group, a silyloxy group, a carbamoyl group, a carbamoyloxy group, a sulfamoyl group, a sulfamoylamino group, a phosphino group, phosphinyl, phosphono group, phosphinyloxy group, phosphonoxy group, phosphinylamino group and a phosophonoamino group.

It is preferred that $X^1$, $X^2$ and $X^3$ respectively represents a divalent group comprising an oxygen atom, and it is more preferred that they respectively represent —O—CO—.

It is preferred that, in the formula (IV), at least one of $X^{21}$, $X^{22}$, $X^{23}$, $R^{21}$, $R^{22}$ and $R^{23}$ comprises an ester bond; more preferred that all of $X^{21}$, $X^{22}$ and $X^{23}$ represent —O—CO— and at least one of $R^{21}$, $R^{22}$ and $R^{23}$ comprises an ester bond; and more preferred that all of $X^{21}$, $X^{22}$, $X^{23}$, $R^{21}$, $R^{22}$ and $R^{23}$ comprise an ester bond.

The compounds represented by the formula (IV) can be produced by reactions of compounds represented by the formula (III) and known esterification agents such as acid chloride, acid anhydride and acid amide. Examples of the organic solvent which can be used in the reactions include halogenated hydrocarbon based organic solvents such as dichloromethane; ester based organic solvents such as methyl acetate and ethyl acetate; ketone based organic solvents such as acetone and methyl ethyl ketone; ether based organic solvents such as tetrahydrofuran and dioxane; nitrile based organic solvents such as acetonitrile and propionyl nitrile; amide based organic solvents such as N,N-dimethylformamide, N,N-dimethylacetamide, 1,3-dimethyl-2-imidazolidone, 1,3-dimethyl-3,4,5,6,-tetrahydro-2(1H)-pyrimidinone (DMPU) and hexamethylphosphoric triamide; and sulfoxide based organic solvents such as dimethyl sulfoxide. And, if necessary, any catalyst or any base may be used.

Specific examples of the compound represented by the formula (IV), which can be produced according to the process of the present invention, are shown below. However, the compounds which can be produced according to the process of the present invention are not to be limited to those shown below.

$(R-X)_m-D$

| | D | m | X | R |
|---|---|---|---|---|
| E-1 | 2,4,6-trimethyl-1,3,5-triazine | 3 | —NH— | aryl with —O—CO—(CH$_2$)$_2$—CO$_2$CH$_3$ and —O—CO—(CH$_2$)$_2$—CO$_2$CH$_3$ |
| E-2 | 2,4,6-trimethyl-1,3,5-triazine | 3 | —NH— | aryl with —O—CO—(CH$_2$)$_3$—CO$_2$CH$_3$ and —O—CO—(CH$_2$)$_3$—CO$_2$CH$_3$ |
| E-3 | 2,4,6-trimethyl-1,3,5-triazine | 3 | —NH— | aryl with —O—CO—(CH$_2$)$_4$—CO$_2$CH$_3$ and —O—CO—(CH$_2$)$_4$—CO$_2$CH$_3$ |
| E-4 | 2,4,6-trimethyl-1,3,5-triazine | 3 | —NH— | aryl with —O—CO—(CH$_2$)$_5$—CO$_2$CH$_3$ and —O—CO—(CH$_2$)$_5$—CO$_2$CH$_3$ |
| E-5 | 2,4,6-trimethyl-1,3,5-triazine | 3 | —NH— | aryl with —O—CO—(CH$_2$)$_6$—CO$_2$CH$_3$ and —O—CO—(CH$_2$)$_6$—CO$_2$CH$_3$ |
| E-6 | 2,4,6-trimethyl-1,3,5-triazine | 3 | —NH— | aryl with —O—CO—(CH$_2$)$_8$—CO$_2$CH$_3$ and —O—CO—(CH$_2$)$_8$—CO$_2$CH$_3$ |
| E-7 | 2,4,6-trimethyl-1,3,5-triazine | 3 | —NH— | aryl with —O—CO—(CH$_2$)$_2$—CO$_2$(CH$_2$CH$_2$O)$_2$C$_6$H$_{13}$ and —O—CO—(CH$_2$)$_2$—CO$_2$(CH$_2$CH$_2$O)$_2$C$_6$H$_{13}$ |

-continued

| | D | m | X | R |
|---|---|---|---|---|
| E-8 | triazine | 3 | —NH— | phenyl-O-CO-(CH$_2$)$_3$-CO$_2$(CH$_2$CH$_2$O)$_2$C$_6$H$_{13}$ / O-CO-(CH$_2$)$_3$-CO$_2$(CH$_2$CH$_2$O)$_2$C$_6$H$_{13}$ |
| E-9 | triazine | 3 | —NH— | phenyl-O-CO-(CH$_2$)$_4$-CO$_2$(CH$_2$CH$_2$O)$_2$C$_6$H$_{13}$ / O-CO-(CH$_2$)$_4$-CO$_2$(CH$_2$CH$_2$O)$_2$C$_6$H$_{13}$ |
| E-10 | triazine | 3 | —NH— | phenyl-O-CO-(CH$_2$)$_6$-CO$_2$(CH$_2$CH$_2$O)$_2$C$_6$H$_{13}$ / O-CO-(CH$_2$)$_6$-CO$_2$(CH$_2$CH$_2$O)$_2$C$_6$H$_{13}$ |
| E-11 | triazine | 3 | —NH— | phenyl-O-CO-(CH$_2$)$_2$-CO$_2$C$_2$H$_5$ / O-CO-(CH$_2$)$_2$-CO$_2$C$_2$H$_5$ |
| E-12 | triazine | 3 | —NH— | phenyl-O-CO-(CH$_2$)$_2$-CO$_2$C$_8$H$_{17}$ / O-CO-(CH$_2$)$_2$-CO$_2$C$_8$H$_{17}$ |
| E-13 | triazine | 3 | —NH— | phenyl-O-CO-(CH$_2$)$_2$-CO$_2$C$_{12}$H$_{25}$ / O-CO-(CH$_2$)$_2$-CO$_2$C$_{12}$H$_{25}$ |
| E-14 | triazine | 3 | —NH— | phenyl-O-CO-(CH$_2$)$_2$-CO$_2$-CH$_2$-CH(C$_2$H$_5$)-C$_4$H$_9$ / O-CO-(CH$_2$)$_2$-CO$_2$-CH$_2$-CH(C$_2$H$_5$)-C$_4$H$_9$ |
| E-15 | triazine | 3 | —NH— | phenyl-O-CO-(CH$_2$)$_2$-CO$_2$CH$_2$CH$_2$C$_8$F$_{17}$ / O-CO-(CH$_2$)$_2$-CO$_2$CH$_2$CH$_2$C$_8$F$_{17}$ |
| E-16 | triazine | 3 | —NH— | phenyl-O-CO-(CH$_2$)$_2$-CO$_2$-cyclohexyl / O-CO-(CH$_2$)$_2$-CO$_2$-cyclohexyl |

-continued

| | D | m | X | R |
|---|---|---|---|---|
| E-17 | triazine | 3 | —NH— | (structure with dimethoxybenzene, two —O—C(=O)—(CH$_2$)$_2$—CO$_2$—phenyl groups) |
| E-18 | triazine | 3 | —NH— | (structure with two —O—C(=O)—(CH$_2$)$_3$—CO$_2$—phenyl groups) |
| E-19 | triazine | 3 | —NH— | (structure with two —O—C(=O)—(CH$_2$)$_8$—CO$_2$—phenyl groups) |
| E-20 | triazine | 3 | —NH— | (structure with two —O—C(=O)—(CH$_2$)$_2$—CO$_2$—C$_6$H$_4$—OCH$_3$ groups) |
| E-21 | triazine | 3 | —NH— | (structure with two —O—C(=O)—C$_6$H$_4$—OC$_8$H$_{17}$ groups) |
| E-22 | triazine | 3 | —NH— | (structure with two —O—C(=O)—C$_6$H$_4$—OC$_{12}$H$_{25}$ groups) |
| E-23 | triazine | 3 | —NH— | (structure with two —O—C(=O)—C$_6$H$_3$(OC$_5$H$_{11}$)$_2$ groups) |

-continued

| | D | m | X | R |
|---|---|---|---|---|
| E-24 | triazine | 3 | —NH— | structure with two ester linkages to benzene rings bearing OC$_8$H$_{17}$ groups |
| E-25 | triazine | 3 | —NH— | structure with two ester linkages to biphenyl groups |
| E-26 | triazine | 3 | —NH— | structure with two ester linkages to phenyl-CO$_2$CH$_3$ groups |
| E-27 | triazine | 3 | —NH— | structure with two ester linkages to cyclohexyl-CO$_2$CH$_3$ groups |
| E-28 | triazine | 3 | —NH— | structure with two ester linkages to phenyl-OCH$_2$-phenyl groups |
| E-29 | triazine | 3 | —NH— | structure with two ester linkages to phenyl-CN groups |
| E-30 | triazine | 3 | —NH— | structure with two ester linkages to phenyl-F groups |
| E-31 | triazine | 3 | —NH— | phenyl-O-CO-(CH$_2$)$_2$-CO$_2$CH$_3$ |

-continued

| | D | m | X | R |
|---|---|---|---|---|
| E-32 | triazine | 3 | —NH— | —C$_6$H$_4$—O—C(O)—(CH$_2$)$_3$—CO$_2$CH$_3$ |
| E-33 | triazine | 3 | —NH— | —C$_6$H$_4$—O—C(O)—(CH$_2$)$_4$—CO$_2$CH$_3$ |
| E-34 | triazine | 3 | —NH— | —C$_6$H$_4$—O—C(O)—(CH$_2$)$_5$—CO$_2$CH$_3$ |
| E-35 | triazine | 3 | —NH— | —C$_6$H$_4$—O—C(O)—(CH$_2$)$_6$—CO$_2$CH$_3$ |
| E-36 | triazine | 3 | —NH— | —C$_6$H$_4$—O—C(O)—(CH$_2$)$_8$—CO$_2$CH$_3$ |
| E-37 | triazine | 3 | —NH— | —C$_6$H$_4$—O—C(O)—(CH$_2$)$_2$—CO$_2$(CH$_2$CH$_2$O)$_2$C$_6$H$_{13}$ |
| E-38 | triazine | 3 | —NH— | —C$_6$H$_4$—O—C(O)—(CH$_2$)$_3$—CO$_2$(CH$_2$CH$_2$O)$_2$C$_6$H$_{13}$ |
| E-39 | triazine | 3 | —NH— | —C$_6$H$_4$—O—C(O)—(CH$_2$)$_4$—CO$_2$(CH$_2$CH$_2$O)$_2$C$_6$H$_{13}$ |
| E-40 | triazine | 3 | —NH— | —C$_6$H$_4$—O—C(O)—(CH$_2$)$_6$—CO$_2$(CH$_2$CH$_2$O)$_2$C$_6$H$_{13}$ |

-continued

| | D | m | X | R |
|---|---|---|---|---|
| E-41 | triazine | 3 | —NH— | –C6H4–O–C(=O)–(CH2)2–CO2C2H5 |
| E-42 | triazine | 3 | —NH— | –C6H4–O–C(=O)–(CH2)2–CO2C8H17 |
| E-43 | triazine | 3 | —NH— | –C6H4–O–C(=O)–(CH2)2–CO2C12H25 |
| E-44 | triazine | 3 | —NH— | –C6H4–O–C(=O)–(CH2)2–CO2–CH2–CH(C2H5)–C4H9 |
| E-45 | triazine | 3 | —NH— | –C6H4–O–C(=O)–(CH2)2–CO2CH2CH2C8F17 |
| E-46 | triazine | 3 | —NH— | –C6H4–O–C(=O)–(CH2)2–CO2–cyclohexyl |
| E-47 | triazine | 3 | —NH— | –C6H4–O–C(=O)–(CH2)2–CO2–C6H5 |
| E-48 | triazine | 3 | —NH— | –C6H4–O–C(=O)–(CH2)3–CO2–C6H5 |
| E-49 | triazine | 3 | —NH— | –C6H4–O–C(=O)–(CH2)8–CO2–C6H5 |

-continued $(R-X)_m-D$

| | D | m | X | R |
|---|---|---|---|---|
| E-50 | triazine | 3 | —NH— | -C6H4-O-C(=O)-(CH2)2-CO2-C6H4-OCH3 |
| E-51 | triazine | 3 | —NH— | -C6H4-O-C(=O)-C6H4-OC8H17 |
| E-52 | triazine | 3 | —NH— | -C6H4-O-C(=O)-C6H4-OC12H25 |
| E-53 | triazine | 3 | —NH— | -C6H4-O-C(=O)-C6H4(m-OC5H11) |
| E-54 | triazine | 3 | —NH— | -C6H4-O-C(=O)-C6H4(m-OC8H17) |
| E-55 | triazine | 3 | —NH— | -C6H4-O-C(=O)-C6H4-C6H5 |
| E-56 | triazine | 3 | —NH— | -C6H4-O-C(=O)-C6H4-CO2CH3 |
| E-57 | triazine | 3 | —NH— | -C6H4-O-C(=O)-C6H10-CO2CH3 |
| E-58 | triazine | 3 | —NH— | -C6H4-O-C(=O)-C6H4-OCH2-C6H5 |

-continued

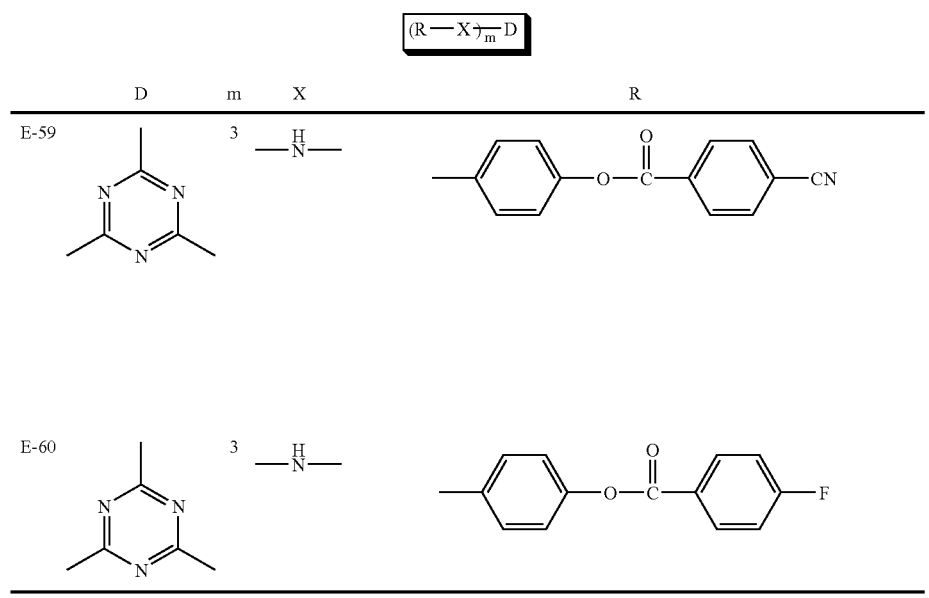

EXAMPLES

The present invention will further be detailed referring to specific Examples. Materials, reagents, amount of use and ratio thereof, manipulation and so forth may appropriately be modified without departing from the spirit of the present invention. It is to be understood that the scope of the present invention is by no means limited to the specific examples described below.

Example No. 1

Preparation of 2,4,6-tris(4'-hydroxyphenylamino)-1,3,5-triazine (III-a)

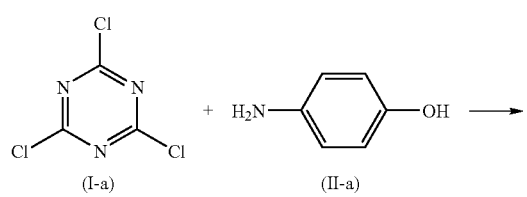

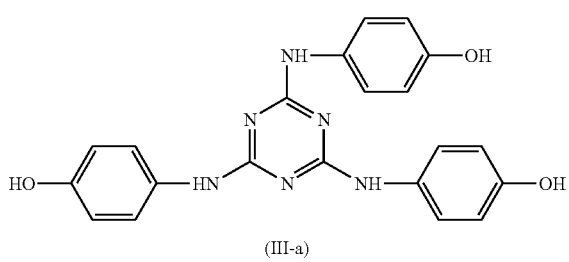

In a 300 ml three-neck flask equipped with a stirrer, a thermometer and a dropping funnel, 3.68 g (0.02 mol) of cyanuric chloride was dissolved in 60 ml of methyl ethyl ketone. Subsequently, 6.55 g (0.06 mol) of p-aminophenol was added slowly to the solution at an inner temperature not higher than 5° C. After the addition, the solution was stirred for 30 minute, and 30 ml of an aqueous solution of 4.92 g (0.06 mol) sodium acetate was added dropwise to the solution with keeping an inner temperature of 10° C. After the dropwise addition, the solution was stirred for 30 minutes at room temperature and was reacted with refluxing for 3 hours. During the reaction, the mixed solvent of methyl ethyl ketone and water was separated into two phases. When the reaction was complete, the reaction solution was poured into 500 ml of ice water to be crystallized. After the filtration, the obtained crystal was washed once with a weakly alkaline solution and twice with 500 ml of water, and dried, to give 7.6 g of a target compound in a 95% yield.

The chemical structure of the product was confirmed by NMR spectrum and MS spectrum.

Comparative Example No. 1

The reaction was carried out in the same manner as Example No. 1, except that potassium carbonate powder was used in the place of the aqueous solution of the sodium acetate and only methyl ethyl ketone was used as reaction solvent. Although the reaction solution was refluxed for 48 hours, the reaction was not complete. When the reaction was complete, the reaction solution was poured into 500 ml of ice water to be crystallized. After the filtration, the obtained crystal was washed and dried to give 5.6 g of a target compound in a 70% yield.

Example No. 2

Preparation of Compound E-31

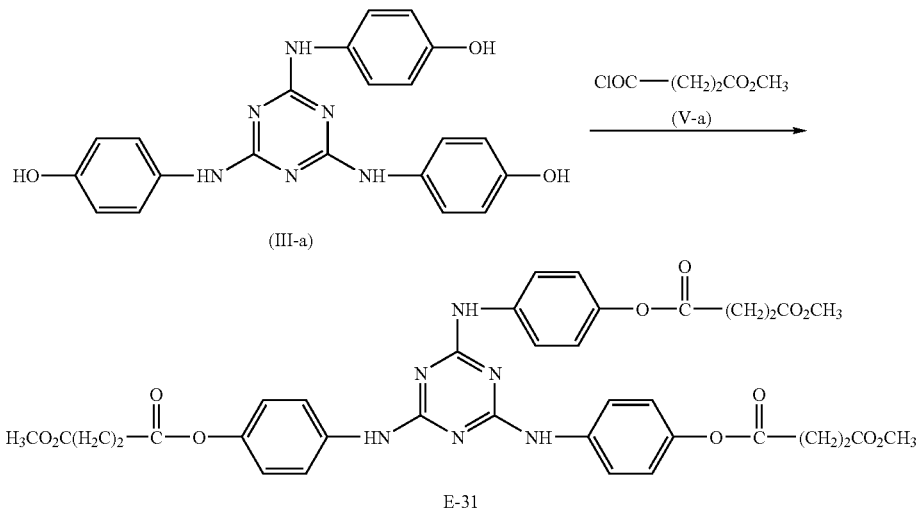

In a 300 ml three-neck flask equipped with a stirrer, a thermometer and a dropping funnel, 32.3 g (0.08 mol) of 2,4,6-tris(4'-hydroxy phenylamino)-1,3,5-triazine (III-a), prepared in Example No. 1, and 0.4 g of dimethylamino pyridine were dissolved in 200 ml of dimethylacetamide. Subsequently, 43.4 g (0.288 mol) of Compound (V-a) was added dropwise to the solution at an inner temperature of not higher than 10° C. After that, 50 ml (0.36 mol) of triethylamine was added dropwise to the solution with keeping an inner temperature of 20° C. After the dropwise addition, the solution was reacted for 5 hours while an inner temperature was kept at room temperature. When the reaction was complete, the reaction solution was poured into 300 ml of water and the organic layer was extracted with 500 ml of ethyl acetate. The extract was washed with water, dried over anhydrous sodium sulfate and evaporated of ethyl acetate under reduced pressure. The obtained residue was purified with silica-gel chromatography (an eluent: n-hexane/ethyl acetate=1/1 volume ratio) to give 50.6 g of a target compound in an 85% yield.

The chemical structure was confirmed by NMR spectrum and MS spectrum.

Example No. 3

Preparation of Compound E-51

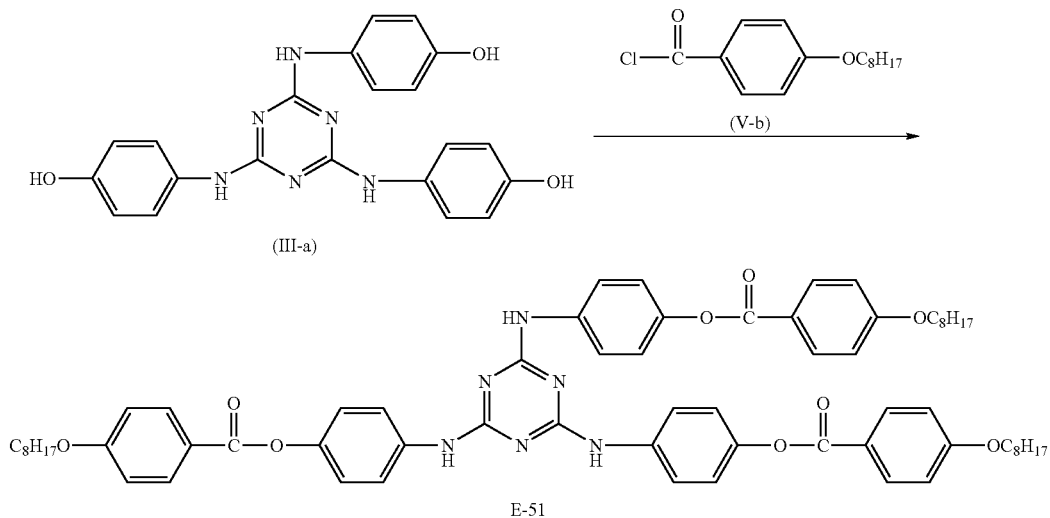

In a 300 ml three-neck flask equipped with a stirrer, a thermometer and a dropping funnel, 12.1 g (0.045 mol) of Compound (V-b) and 0.2 g of dimethylamino pyridine were dissolved in 100 ml of tetrahydrofuran, and, after that, 7.8 ml (0.045 mol) of diisopropylethylamine was added to the solution. A tetrahydrofuran solution of 4.02 g (0.01 mol) of 2,4,6-tris(4-hydroxyphenylamino)-1,3,5-triazine (III-a) was added dropwise to the solution at an inner temperature of not higher than 20° C. After the dropwise addition, the solution was reacted for 6 hours while the inner temperature was kept at room temperature. After the reaction was complete, the reaction solution was poured into 600 ml of methanol to be crystallized. The obtained crystal was washed with methanol and dried to give 8.8 g of a target compound in an 80% yield.

The chemical structure was confirmed by NMR spectrum and MS spectrum.

As described the above, it was found that, according to the process of the present invention, 2,4,6-tris(hydroxyphenylamino)-1,3,5-triazines can be obtained not only in a higher yield (more selectively) but also in a shorter time as compared with the conventional process employing a base and only an organic solvent.

Having described our invention as related to the present embodiments, it is our intention that the invention not be limited by any of the details of the description, unless otherwise specified, but rather be construed broadly within its spirit and scope as set out in the accompanying claims.

What is claimed is:

1. A process for producing 2,4,6-tris(hydroxyphenylamino)-1,3,5-triazine comprising:
    reacting a compound represented by a formula (I) and a compound represented by a formula (II) at a temperature falling within a range from −10 to 10°C. in an aprotic solvent, and
    adding a water solution of a base thereto at a temperature falling within a range from −10 to 10°C., and heating or refluxing to produce a compound represented by a formula (III):

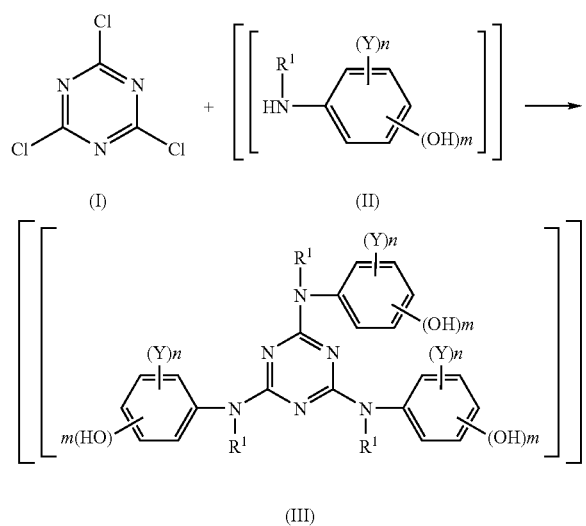

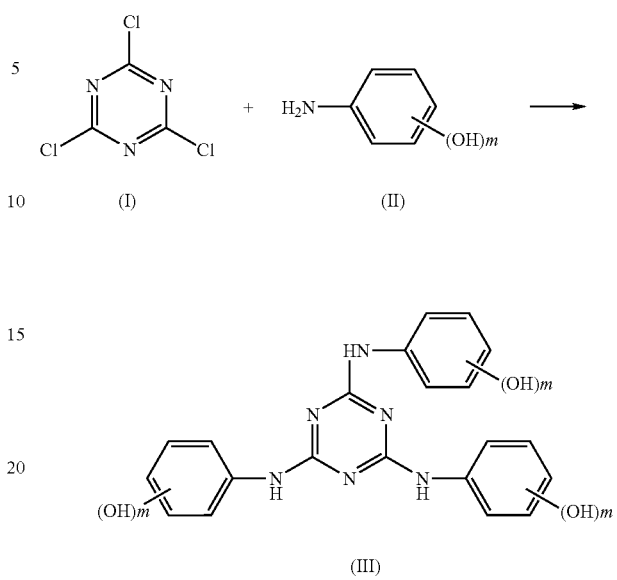

where m is an integer from 1 to 5.

2. The process of claim 1, wherein the aprotic solvent and the water solution have separated into two phases at least when the reaction is complete.

3. The process of claim 1, wherein the base is an inorganic base.

4. The process of claim 1, wherein at least one alkali metal salt is used as the base.

5. The process of claim 1, wherein the base is sodium acetate.

6. The process of claim 1, wherein the aprotic solvent is selected from the group consisting of aromatic compounds, ethers, ketones and esters.

7. The process of claim 1, wherein the reaction is carried out for a time falling within the range from 30 minutes to 10 hours.

8. The process of claim 1, wherein, after adding the water solution of a base, the reaction is carried out under heating.

9. The process of claim 1, further comprising mixing a solution of the compound represented by the formula (I) and a solution of the compound represented by the formula (II) at a temperature of not higher than 10°C.

10. The process of claim 1, wherein the water solution of a base is added dropwise to a solution of the compound represented by the formula (I) and the compound represented by the formula (II) in said aprotic solvent.

11. The process of claim 1, wherein, after adding the water solution of a base, the reaction is carried out under refluxing.

* * * * *